United States Patent
Hanlon

(10) Patent No.: US 7,530,354 B2
(45) Date of Patent: May 12, 2009

(54) DISTENDING NASAL AIR FILTER

(76) Inventor: Mark Douglas Hanlon, 4 Strout La., Durham, NH (US) 03824

(*) Notice: Subject to any disclaimer, the term of this patent is extended or adjusted under 35 U.S.C. 154(b) by 572 days.

(21) Appl. No.: 11/097,702

(22) Filed: Apr. 4, 2005

(65) Prior Publication Data

US 2006/0219247 A1   Oct. 5, 2006

(51) Int. Cl.
A62B 7/00 (2006.01)

(52) U.S. Cl. .......... 128/206.18; 128/206.14; 128/206.19

(58) Field of Classification Search .......... 128/201.17, 128/205.27, 205.29, 206.11, 200.24, 206.18, 128/205.28, 206.16, 206.17, 206.19, 206.14, 128/204.13, 205.25, 206.12, 207.12, 203.29; 602/48, 74; 55/279, 524, DIG. 35; 606/199, 606/204.4

See application file for complete search history.

(56) References Cited

U.S. PATENT DOCUMENTS

| | | | | |
|---|---|---|---|---|
| 1,925,764 A * | 9/1933 | Le Duc | ............... | 128/206.12 |
| 2,070,754 A * | 2/1937 | Schwartz | ............... | 128/206.12 |
| 2,296,150 A * | 9/1942 | Dockson et al. | ............... | 128/206.12 |
| 2,296,775 A * | 9/1942 | Dockson | ............... | 128/206.12 |
| 2,318,790 A * | 5/1943 | Martindale et al. | ............... | 128/206.16 |
| 2,556,589 A * | 6/1951 | Le Duc | ............... | 128/206.12 |
| 2,572,254 A * | 10/1951 | Folberth | ............... | 128/206.18 |
| 2,634,724 A * | 4/1953 | Burns | ............... | 128/206.19 |
| 3,049,121 A * | 8/1962 | Brumfield et al. | ............... | 128/206.14 |
| 3,750,665 A * | 8/1973 | Stranicky | ............... | 128/206.12 |
| 3,774,601 A * | 11/1973 | Langone | ............... | 128/205.29 |
| 4,004,584 A * | 1/1977 | Geaney | ............... | 128/206.14 |
| 4,038,979 A * | 8/1977 | McCosker | ............... | 128/206.12 |
| 4,240,420 A * | 12/1980 | Riaboy | ............... | 128/206.14 |
| 4,354,489 A * | 10/1982 | Riaboy | ............... | 128/206.14 |
| 4,503,851 A * | 3/1985 | Braunroth | ............... | 128/203.29 |
| 4,520,509 A * | 6/1985 | Ward | ............... | 2/206 |
| 4,534,342 A * | 8/1985 | Pexa | ............... | 602/74 |
| 4,628,927 A * | 12/1986 | Ward | ............... | 128/206.17 |
| 4,726,365 A * | 2/1988 | Jablonski | ............... | 128/202.13 |
| 4,790,307 A * | 12/1988 | Haber et al. | ............... | 128/206.19 |
| 4,856,509 A * | 8/1989 | Lemelson | ............... | 128/206.19 |
| 4,977,634 A * | 12/1990 | Koji | ............... | 5/638 |
| 4,984,302 A * | 1/1991 | Lincoln | ............... | 2/206 |
| 5,392,773 A * | 2/1995 | Bertrand | ............... | 128/206.11 |
| 5,485,836 A * | 1/1996 | Lincoln | ............... | 128/206.11 |
| 5,570,684 A * | 11/1996 | Behr | ............... | 128/201.13 |
| 5,636,629 A * | 6/1997 | Patterson, Jr. | ............... | 128/207.13 |
| 5,706,804 A * | 1/1998 | Baumann et al. | ............... | 128/206.19 |
| 5,727,544 A * | 3/1998 | Miura | ............... | 128/201.13 |
| 5,740,798 A * | 4/1998 | McKinney | ............... | 128/206.18 |
| 5,941,244 A * | 8/1999 | Yamazaki et al. | ............... | 128/206.19 |
| 6,098,624 A * | 8/2000 | Utamaru | ............... | 128/206.18 |

(Continued)

Primary Examiner—Steven O Douglas

(57) ABSTRACT

A piece of shear plastic of approximate size and shape to cover human nose and upper lip, with a filter element installed therein at an opening located at the nostrils. Adhesive added to the rear of the housing for airtight seal when applied to the nose and upper lip, so that all air breathed through the nose goes through the filter element. An aluminum strip at the bridge of the nose is added to help conform to the nose. The plastic housing is perforated to allow human perspiration to seep through the housing. Scoring is made during manufacturing in the area approximately at the side of the human nose so that the invention may be pinched to conform to the nose of the wearer. The filter element inserted into the plastic housing at the nostrils, is elongated and rolled back during manufacturing to allow the wearer to reveal additional filter element should it be required.

8 Claims, 2 Drawing Sheets

U.S. PATENT DOCUMENTS

| | | | |
|---|---|---|---|
| 6,176,239 B1 * | 1/2001 | Grove et al. | 128/206.24 |
| 6,216,694 B1 * | 4/2001 | Chen | 128/206.11 |
| 6,532,598 B1 * | 3/2003 | Cardarelli | 2/173 |
| 6,543,450 B1 * | 4/2003 | Flynn | 128/206.19 |
| 6,742,518 B2 * | 6/2004 | Chang | 128/205.29 |
| 6,886,563 B2 * | 5/2005 | Bostock et al. | 128/206.19 |
| 7,107,990 B2 * | 9/2006 | Lee | 128/205.25 |
| 7,185,653 B2 * | 3/2007 | Lee | 128/206.19 |
| 2002/0166556 A1 * | 11/2002 | Jacob | 128/206.11 |
| 2003/0183233 A1 * | 10/2003 | Chang | 128/205.29 |
| 2004/0089303 A1 * | 5/2004 | Chien | 128/206.11 |
| 2005/0161046 A1 * | 7/2005 | Michaels | 128/206.14 |
| 2005/0183727 A1 * | 8/2005 | Chou | 128/206.19 |
| 2006/0011201 A1 * | 1/2006 | Ku | 128/206.19 |
| 2006/0201513 A1 * | 9/2006 | Chu | 128/206.19 |
| 2007/0079830 A1 * | 4/2007 | Edwards et al. | 128/205.27 |

* cited by examiner

DISTENDING NASAL AIR FILTER

CROSS-REFERENCE TO RELATED APPLICATIONS

60/414,799

FEDERALLY SPONSORED RESEARCH non applicable

NAMES OF PARTIES TO JOINT RESEARCH AGREEMENT

Not Applicable

INCORPORATION BY REFERENCE OF MATERIAL SUBMITTED ON A COMPACT DISC

Not Applicable

BACKGROUND OF THE INVENTION

1. Field of Invention

This invention relates to a an contour nasal air filter that is strong and relatively inconspicuous; it adheres to the contours of the nose and upper lip creating an airtight bond, with a single expandable filter element located at the nostril area that may be distended by pulling the filter element out and away from the user, revealing new filter element needed to replace clogged element or creating a larger reservoir of air within the filter element enabling unrestricted heavy breathing during an emergency.

2. Background of the Invention

Commonly supplied face masks used to filter out particles or contaminates from the air are generally made of a rigid filter element that comprises the entire mask (housing and filter element) that is connected to the head by an elastic band (generally used by building contractors) or by a cloth like material that covers the nose and mouth and straps around the ears (generally used by physicians and health care providers). These masks are intended for occupational uses as opposed to emergency uses such as the instant invention.

Prior inventions in common use cover both the nose and the mouth. Because these inventions use the filter element itself as both the filter and the housing for the filter, the filter is not bonded to the skin of the wearer. Further, once the filter becomes clogged with Contaminants it must be removed. These prior inventions are generally white in color and cover most of the face. As such they are conspicuous to other persons. The characteristics of these common masks do not resemble the characteristics of the instant invention.

Thereafter, some inventors created a human nose filter that contain a filter that covers only the nostrils. U.S. Pat. Nos. 4,984,302 (1991) and 5,485,836 (1996) to Lincoln disclose a device that attaches to the nose and filters the air a person breathes through the nose. The filter element is attached to the nose by two rectangular adhesive strips that project from the filter element at the nostrils up the side of the nose. However, the filter element itself is the size of the human nostrils and may, depending upon the situation, clog with contaminants quickly. Additionally, there is no reservoir within the filter element to allow the wearer to breath easily. Finally, the filter element has no secure housing and may fail in an emergency due to perspiration. The current invention contains a reservoir of filter element that may be distended out by the wearer to reveal additional filter element if the wearer is breathing heavily or if the contaminants in the air block the filter. The housing of the filter element is durable and pliable and uses the nose itself for structural support.

Further inventions attempt to seal the nose so that only filtered air is breathed. U.S. Pat. No. 5,392,773 (1995) to Bertrand, discloses a simple filter mesh element to cover the nose with adhesive tabs attached to the area surrounding the nostrils but leaving the upper surface of the nose exposed. Again, this method does not provide sufficient filter media to allow the wearer to breath heavily in an emergency nor does the smaller filter element prevent quick saturation of the filter element by contaminants, debris or human perspiration, causing the mask to fail in an emergency.

The prior patents of Lincoln and Bertrand lack a secure housing to provide for extensive breathing, perspiration, and movement likely to occur in an emergency.

Other devices include U.S. Pat. No. 6,098,624 (2000) to Utamaru, which discloses an adhesive strip with two gauze filters inserted therein to cover the nostril opening. As with the prior devices, the housing is only an adhesive strip that is pressed against the sides of the nose and cheek. This housing lacks sufficient structure for emergency use. The filter is limited to a single layer at each nostril. This small filter will contaminate quickly and prevent its use once clogged. The same may be said for U.S. Pat. No. 6,216,694 (2001) to Chen. In the Chen patent, the filter element is in stuffed into the nose. Once clogged the filter is useless. The housing of the instant invention relies upon several structural components to prevent failure during the panic and trauma of an emergency. With the instant invention, the entire structure of the human nose is used for support and adhesion. Unlike prior inventions using small strips of adhesive tape to secure the filter to the nose, this invention contains a built in aluminum strip situated at the bridge of the nose for additional support, and the entire unit adheres to the nose. Upon applying this invention to the nose, this strip is contoured to the nose by the wearer. The adhesive seal consists of the entire housing excluding only the filter, for proper adhesion. Again, prior inventions rely either upon strips of adhesive tape, or rubber bands. All of which are insufficient for emergency use. This is the first nasal air filter designed to be effective during an emergency yet it permits the wearer to use their mouth freely.

Prior nasal air filters designed to apply to the human head are quite noticeable to persons viewing the wearer. The instant patent is flesh colored, thin, and skin like. It is applied to the nose of the wearer only. This nasal air filter covers the nose like a second layer of skin and is distinguishable to third parties only upon close inspection. The wearer will not be as conspicuous to others as they would with other types of breathing filters applied to the human head.

Other inventions designed to be applied to the human head to aid the filtering of air, are applied by elastic strap around the head or ears of the wearer, again causing the apparatus to be conspicuous, and preventing the use of eyeglasses and other head gear.

This invention is applied to the nose and upper lip only, and permits the user to wear glasses or any other kind of head gear without interference.

When the wearer has concluded the task requiring this nasal air filter, the user simply peels the filter off, and discards it in the pouch that the product was supplied in. Once sealed, the product may be safely discarded.

Other nasal air filters do not fit tightly to the face. The instant invention contains a pinch pleat at each side to fit the nose securely, and contour to the nose.

OBJECTS AND ADVANTAGES

Accordingly, several objects and advantages of the present invention are:
(a) to provide a nasal air filter that attached to the entire nose for strength and durability in an emergency;
(b) to provide a nasal air filter that attaches to the human nose by adhesion and not by strap;
(c) to provide a nasal air filter that attaches to the human head, by covering the nose and nostrils only, allowing the human to breath filtered air normally through the nose;
(d) to provide a nasal air filter that is sheer and pliable adhering to the contours of the human nose like skin through the use of pinch pleat type construction;
(e) to provide a nasal air filter device that when attached to the human nose creates an air tight seal, so that the only air passable through the device passes through the built in distending air filter element to ensure that the air breathed through the nose is filtered;
(f) to provide a nasal air filter device with a built in aluminum strip located at the bridge of the nose which is formed to the contour of the nose of the wearer during application to ensure the durability of the attachment;
(g) to provide a nasal air filter device that attaches to the human nose through the use of preapplied adhesive and creates a seal around the human nose, quickly, easily and with little or no instruction;
(h) to provide a wearable air filter device that attaches to the human nose and is made of plastic that is pigmented to approximately match the color of human skin to make the device nearly undetectable from a distance;
(i) to provide a wearable air filter device that attaches to the human nose that contains a filter element that is folded and may be distended by the wearer during an emergency to allow for the heavy breathing, perspiration, and sputum that the wearer may experience during an emergency and to provide a reserve of filter media that may be needed in heavy contamination or debris circumstances;
(j) to provide a nasal air filter device that attaches to the human nose that when purchased will be in a foil type pouch, flat, and will fit within the wearers wallet, purse, pocket, easily without inconvenience, and when done, may be returned to that same pouch, sealed, and disposed of safely.
(k) to provide a nasal air filter device with a filter made of a synthetic media of melt blown layers sandwiched between two outer layers of synthetic spun bond impregnated with activated charcoal to remove odors.
Still further objects and advantages will become apparent from a consideration of the ensuing description and drawings.

SUMMARY

A human nasal air filter, made of a flexible housing sufficient to substantially cover the contours of the human nose and upper lip with a single filter element located approximately at the nostril Area which may be distended to assist the wearer to breath easily and substantially free of bacteria, virus, pollen, and other contaminants through the human nose; Because the invention is attached only to the nose and upper lip of the wearer, the wearer's mouth is uncovered and the nose is substantially sealed to outside air, except through the filter of the invention; For removal by wearer the invention is peeled off the nose by the wearer by hand in seconds, and disposed.

BRIEF DESCRIPTION OF THE SEVERAL VIEWS

DRAWINGS

Reference Numerals

| | |
|---|---|
| 10 housing front | 12 rounded edges |
| 14 scoring for pleats | 16 aluminum strip |
| 18 filter opening front | 20 filter frontal view |
| 22 housing rear | 24 filter opening rear |
| 26 filter | 28 reserve filter |
| 30 perforations | |

DETAILED DESCRIPTION FIGS. 1,3

Preferred Embodiment

Figure 1:
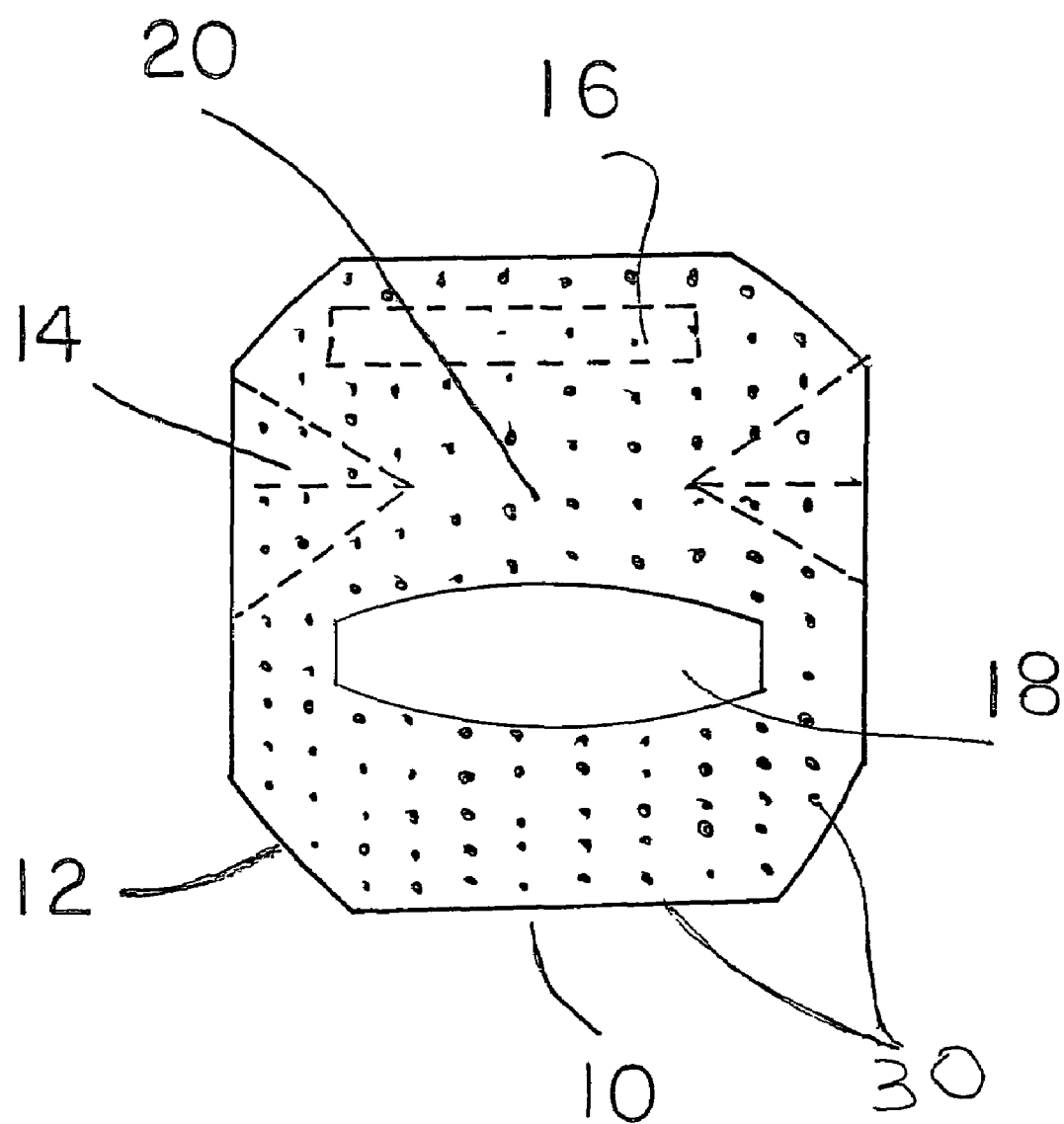
FIG. 1 is a perspective view illustrating the flexible housing of a distending nasal air filter according to the present invention, unfolded without the filter element installed, and depicting a multitude of small perforations in the housing to allow human perspiration to escape.

A preferred embodiment of the invention is illustrated at FIG. 1 and FIG. 3. FIG. 1 shows the housing 10 of the invention which is made of a thin layer of plastic that is pigmented to match human skin. The plastic housing is cut during the manufacturing process so that it has substantially rounded edges 12, with a v-shape at each side of the housing that comprise the pleat pattern 14 cut into the back of the plastic housing at the time of manufacturing.

Inserted into the housing 10 substantially at the top of the invention is a sheer aluminum strip 16 approximately 4.5 millimeters in width and ½ millimeter in height. The housing size 10 is large enough to cover all or most of the bridge of the human nose and the upper lip, leaving the filter opening 18 substantially at the nostrils.

During the manufacturing process, a flat rectangular filter media is folded lengthwise creating a long cone that now has a diameter equal to the opening in the housing. The lengthwise seam is bonded closed as is the seam at the top of the cone. The filter media is inserted through the opening in the housing with only a small portion extending beyond the rear of the housing. That portion is folded over the rear of the housing and bonded to the housing. The filter element is then rolled back during manufacturing only to be distended by the wearer should additional filter element be required.

Figure 2:
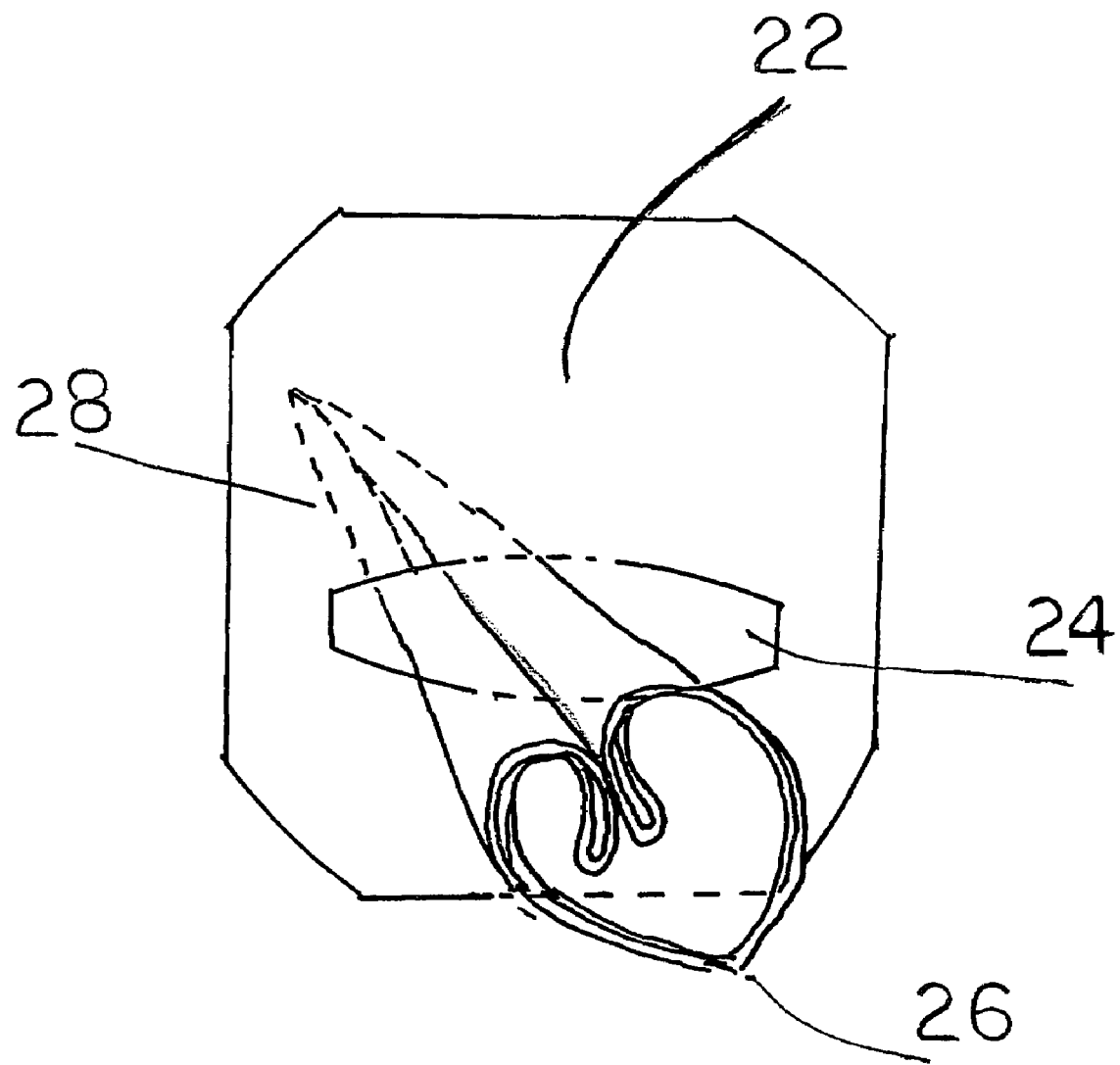
FIG. 2 is a perspective view illustrating a distending nasal air filter according to the present invention, unfolded with the filter element inserted into the opening of the plastic housing.

Operation—FIGS. 1, 2, 3

When the wearer first takes the invention out of its packaging, it is flat 10 (FIG. 1). Applied to the rear of the housing 22 (FIG. 2) is a non-toxic adhesive that is covered with a removable plastic sheeting. The user removes this plastic from the rear of the invention then places rear and top of the invention to the bridge of the nose. The invention must be applied to the nose so that the filter element is located as the nostrils. Therefore, if the wearer has a small nose, the top portion of the invention will be placed high on the bridge of the nose to allow the filter element to be placed over the nostrils. If the user has a large nose, the tip of the invention is set lower on the bridge of the nose to locate the filter at the nostrils.

Inserted into the housing 10 substantially at the top of the invention is a sheer aluminum strip 16. This thin aluminum strip is situated on the bridge of the nose by the wearer, and held in place with one hand, while the other hand checks to see that the location of the invention on the bridge of the nose is high or low enough so that the filter element is substantially over the nostrils. when the wearer adjusts the location of the aluminum strip to the correct height, the wearer bends the strip over the bridge of the nose, so that the aluminum strip conforms to the shape of the nose. This gives the invention strength and position. The wearer then seals the invention to the bridge of the nose by pressing down on the housing which contains an adhesive. The wearer next takes the thumb and forefinger and pinches the pleats 14 located on each side of the invention, to snug the housing to the side of the wearers nose. The pleat backing is also covered with adhesive sealing the pleats together and snug to the nose. The wearer then presses the remainder of the housing to the nose and upper lip, forming a seal around the nose and leaving the filter opening 18 which contains the filter element at the nostrils.

The wearer may then adjust the filter element for comfort by distending the filter element out to obtain a reservoir form which the wearer draws air to breath. Should the wearer require additional filter due to heavy exertion or should the filter element become clogged by particulates from fire, dust, or pollen, the reserve element may be rolled out to reveal fresh element that may be breather through.

FIG. 3 depicts the filter element 26 of the invention. The filter element consists of a substantially synthetic media, substantially layered with one or more layers of melt blown polypropylene or substantially similar material 32, which is placed between two sheets of spun bond polypropylene 30, or substantially similar element, all of varying thickness to achieve on or more of particle filtration, micro filtration or ultra filtration, dependent upon the filtration task. In circumstances where the filtration of odor is required, the filter element 26 would have activated charcoal 34 added to the melt blown polypropylene to filter out offensive odors, such as rotting corpse odor, and other such offensive odors.

CONCLUSIONS, RAMIFICATION, SCOPE

From the description above, a number of conclusions, ramifications and scope of the invention are as follows:

The invention is small, flat and lightweight and may be kept in the pocket, purse, wallet or pocket of the wearer in the event that use while not previously believed to be necessary, is now necessary as a result of a surprise or emergency.

The invention is shear, and fits over the nose like a second layer of skin.

The invention is flesh colored, and when applied is nearly undetectable from a distance, and is not alarming when viewed up close.

The invention has an adjustment feature, pleats, to adjust to the contours of the nose and cheeks of the wearer thus enabling the invention to be worn by wearers with different sized noses and facial features.

The invention adheres to the face with adhesive forming an airtight seal to the skin ensuring that the only air breathed by the wearer is through the filter element.

The filter element may be specialized to target specific contaminants to be removed, e.g., specific bacteria, virus, gases, etc.

The invention is disposable, so that the wearer simply peels the invention off of the face after the task or emergency is complete and discard the invention.

The inventions does not interfere with clothing or head gear of the wearer as it has no straps that wrap around the ears or head, as do other devices.

The invention does not interfere with the users ability to speak through the mouth should that be required.

The filter element is expandable to allow progressive utilization, as the part of the filter that is exposed to the air becomes clogged with debris and contaminants, the user expands the filter to reveal additional new filter element.

Although the description above contains many specifications, these should not be construed as limiting the scope of the invention but as merely providing illustrations of some of the presently preferred embodiments of this invention. For example, the entire unit may vary in size with a child's unit being smaller than that of an adult; The shape of the pleats may vary; The overall shape of the housing may vary; the shape of the filter element and the element material may vary.

Thus, the scope of the invention should be determined by the appended claims and their legal equivalents, rather than by the examples given.

I claim:

1. A distending nasal air filter device, comprising:
   (a) a flexible housing adapted to approximately cover the entire human nose and upper lip of the wearer, with a substantially round opening of a predetermined size cut into said housing and located at a bottom portion of said flexible housing so as to be adapted to be disposed at an area where the user's nostrils are intended to be,
   (b) a single separate filter element adapted to be removably attached to said flexible housing in a rolled configuration at said opening located approximately at the nostrils of the wearer,
   (c) a means adapted for substantially attaching said flexible housing approximately to the human nose and upper lip of the wearer, whereby the human wearer has the mouth uncovered and whereby the nose is substantially sealed to outside air, except through the said filter element.

2. The distending nasal air filter device of claim 1 wherein said flexible housing and filter element are pigmented to approximately match human skin color thereby allowing the user to wear the device without detraction from appearance.

3. The distending nasal air filter device of claim 1 wherein the means adapted for substantially attaching said flexible housing to the human nose and upper lip of the wearer, is comprised substantially of non-toxic removable adhesive that is applied during manufacture to a rear of said flexible housing, whereby the wearer may adhere the device to the nose and upper lip creating a seal to outside air except through the said single separate filter element.

4. The distending nasal air filter device of claim 1 wherein said flexible housing during manufacturing is scored at each side of said flexible housing substantially with a horizontal v so that when said v is pinched together by the wearer after applying said nasal air filter to the nose, the flexible housing substantially contours to the shape of the nose of the wearer giving said flexible housing extra strength and seal from unfiltered air.

5. The distending nasal air filter device of claim 1 wherein said flexible housing contains an aluminum strip inserted into a top center of said flexible housing to allow the wearer to bend the strip tight to the nose for greater strength and seal from unfiltered air.

6. The distending nasal air filter device of claim 1 wherein the flexible housing is substantially comprised of a shear plastic of a predetermined thickness, with a multitude of perforations to permit human perspiration to escape.

7. The distending nasal air filter device of claim 1 wherein said single separate filter element is manufactured with at least one extra filter element than is required for immediate use by the wearer, and said at least one extra filter element is folded and kept in reserve by the user until required.

8. The distending nasal air filter device of claim 1 wherein said single separate filter element is manufactured into the shape of an elongated cylinder or cone with a diameter approximately equal to the opening in said flexible housing, with one end of said filter element bonded to a rear of said flexible housing at the location of said opening with the remainder of the elongated filter element protruding through the front of said flexible housing, including a surplus filter element that is folded back toward said flexible housing and kept in place with adhesive substance such that said surplus filter element may be unfolded and made available for use by the wearer if the filter element exposed to the atmosphere becomes clogged or otherwise not functional, thereby increasing the users ability to filter air until an emergency has been abated.

\* \* \* \* \*